US007291614B2

(12) United States Patent
Fine et al.

(10) Patent No.: US 7,291,614 B2
(45) Date of Patent: Nov. 6, 2007

(54) PROCESSES FOR THE PREPARATION OF LINEZOLID INTERMEDIATE

(75) Inventors: Serguei Fine, Qiriat-Arbaa (IL); Tamar Nidam, Yehud (IL); Viviana Braude, Kadima (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 11/361,457

(22) Filed: Feb. 23, 2006

(65) Prior Publication Data
US 2007/0021417 A1 Jan. 25, 2007

Related U.S. Application Data

(60) Provisional application No. 60/690,822, filed on Jun. 14, 2005, provisional application No. 60/656,778, filed on Feb. 24, 2005, provisional application No. 60/656,646, filed on Feb. 24, 2005.

(51) Int. Cl.
*A61K 31/5377* (2006.01)
(52) U.S. Cl. .................................................. 514/236.8
(58) Field of Classification Search .............. 514/236.8
See application file for complete search history.

(56) References Cited

U.S. PATENT DOCUMENTS

| 4,705,799 | A | 11/1987 | Gregory |
| 5,688,792 | A | 11/1997 | Barbachyn et al. |
| 6,333,198 | B1 | 12/2001 | Edmeades et al. |
| 6,444,813 | B2 | 9/2002 | Bergren |
| 6,559,305 | B1 | 5/2003 | Bergren |

FOREIGN PATENT DOCUMENTS

| AU | 2001100437 | 11/2001 |
| CA | 2 168 560 | 8/2001 |
| EP | 0 311 090 | 4/1989 |
| EP | 0 352 781 | 1/1990 |
| EP | 0 717 738 | 10/1999 |
| EP | 0 963 980 | 12/1999 |
| WO | WO 93/09103 | 5/1993 |
| WO | WO 95/07271 | 3/1995 |
| WO | WO 01/57035 | 8/2001 |
| WO | WO 03/093247 | 11/2003 |
| WO | WO 2004/026848 | 4/2004 |
| WO | WO 2005/035530 | 4/2005 |

OTHER PUBLICATIONS

Brickner, et al., "Synthesis And Antibacterial Activity Of U-100592 And U-100766, Two Oxazolidinone Antibacterial Agents For The Potential Treatment Of Multidrug-Resistant Gram-Positive Bacterial Infections", *Journal of Medicinal Chemistry*, vol. 39, No. 3, pp. 673-679, (1996).
Reddy, et al. "Isolation and Characterization of Process-Related Impurities in Linezolid" *Journal of Pharmaceutical and Biomedical Analysis*, vol. 30, pp. 635-642 (2002).

Perrault, et al., "The Synthesis Of N-Aryl-5(S)-Aminoethyl-2-Oxazolidinone Antibacterials And Derivatives In One Step From Aryl Carbamates", *Organic Process Research & Development*, vol. 7, No. 4., pp. 533-546 (2003).
Peng, et al. "Determination of Linezolid In Plasma by Reversed-Phase High-Performance Liquid Chromatography" *Journal of Pharmaceutical and Biomedical Analysis*, vol. 20, pp. 65-73 (1999).
Gregory, et al. "Antibacterials. Synthesis and Structure-Activity Studies of 3-Aryl-2-Oxooxazolidines. 2. The "A" Group." *Journal of Medicinal Chemistry*, vol. 33, No. 9, pp. 2569-2578 (1990).
Gregory, et al. "Antibacterials. Synthesis and Structure-Activity Studies of 3-Aryl-2-Oxooxazolidines. 1. The "B" Group." *Journal of Medicinal Chemistry*, vol. 32, No. 8, pp. 1673-1681 (1989).
Sbardella, et al. "Synthesis and In Vitro Antimycobacterial Activity of Novel 3-(1H-Pyrrol-1-yl)-2-Oxazolidinone Analogues of PNU-100480" *Bioorganic & Medicinal Chemistry Letters*, vol. 14, pp. 1537-1541 (2004).
Emea—European Medicines Agency "ICH Topic Q 3 A (R1)—Impurities in new Drug Substances" CPMP/ICH/2737/99 (2002).
Emea—European Medicines Agency "ICH Topic Q 2 (R1)—Validation of Analytical Procedures: Text and Methodology" CPMP/ICH/381/95 (1995).
Sheradsky "Azides as Synthetic Starting Materials" *The Chemistry of The Azido Group* (Ed. S. Patai) Interscience Publishers, Chapter 6, pp. 331-395 (1971).
*Merck Index*, 13th Edition, Monograph No. 5526, CAS Registry No. 165800-03-3, pp. 986, (2001).
Snyder, et al., *Introduction To Modern Liquid Chromatography*, 2nd Ed., pp. 549-572, John Wiley & Sons, Inc. (1979).
Strobel, et al., *Chemical Instrumentation: A Systematic Approach*, $3^{rd}$ Ed., pp. 391-393, 879-894, 922-952, 953, (1989).
Brittain (Ed.) *Polymorphism in Pharmaceutical Solids*, Drugs and the Pharmaceutical Sciences vol. 95, pp. 1-2, 178-179, 236, Marcel Dekker, Inc. New York, New York, (1999).
Grant "Theory and Origin of Polymorphism" *Polymorphism in Pharmaceutical Solids, Drugs and the Pharmaceutical Sciences* vol. 95 (Ed. Brittain), Marcel Dekker, Inc., pp. 1-33, (1999).
Guillory "Generation of Polymorphs, Hydrates, Solvates, and Amorphous Solids" *Polymorphism in Pharmaceutical Solids, Drugs and the Pharmaceutical Sciences* vol. 95 (Ed. Brittain), Marcel Dekker, Inc., pp. 183-226, (1999).
Byrn, et al., *Solid-State Chemistry Of Drugs*, $2^{nd}$ Ed., p. 4, (1999).
*Perry's Chemical Engineers' Handbook*, $6^{th}$ Ed., pp. 20-54 to 20-57, (1984).
Rouhi, "The Right Stuff", *Chemical & Engineering News*, pp. 32-35, (2003).
*US Pharmacopia # 23, National Formulary # 18*, pp. 1843-1844, (1995).

Primary Examiner—Rebecca Anderson
Assistant Examiner—Shawquia Young
(74) Attorney, Agent, or Firm—Kenyon & Kenyon LLP

(57) ABSTRACT

The present invention provides improved methods of converting R—N-(4-morpholiyl-3-fluorophenyl)-2-oxo-5-oxazolidinyl-methyl azide (III) to the intermediate S—N-(4-morpholinyl-3-fluorophenyl)-2-oxo-5-oxazolidinyl-methyl amine (II) that involve the production of fewer by-products than previous methods. The amine (II) may then be converted into linezolid (I) of high chemical purity with respect to the inactive R-enantiomer and bis-linezolid (IV), and is in high yield, without the need for tedious, complicated purification steps, such as chromatography.

21 Claims, No Drawings

PROCESSES FOR THE PREPARATION OF LINEZOLID INTERMEDIATE

CROSS-REFERENCE TO RELATED APPLICATIONS

This application claims the benefit of provisional application Ser. No. 60/656,778, filed Feb. 24, 2005, Ser. No. 60/656,646, filed Feb. 24, 2005, as well as Ser. No. 60/690,822, filed Jun. 14, 2005 which are incorporated herein by reference.

FIELD OF THE INVENTION

The present invention relates to improved methods of converting the intermediate R—N-(4-morpholinyl-3-fluorophenyl)-2-oxo-5-oxazolidinyl-methyl azide to the intermediate S—N-(4-morpholinyl-3-fluorophenyl)-2-oxo-5-oxazolidinyl-methyl amine, and the use of such methods in the preparation of linezolid.

BACKGROUND OF THE INVENTION

Linezolid [(S)—N—[[3-(3-Fluoro-4-morpholinyl)phenyl]-2-oxo-5-oxazolidinyl]methyl] acetamide] is an antimicrobial agent. Linezolid is an oxazolidinone, having the empirical formula $C_{16}H_{20}FN_3O_4$ and the following structure (I):

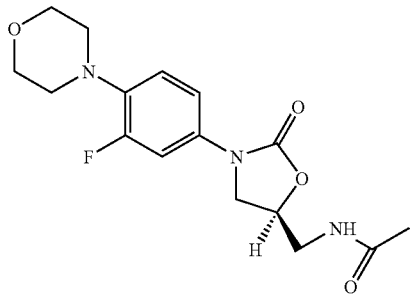

Linezolid is described in The Merck Index (13th edition, Monograph number: 05526, CAS Registry Number: 165800-03-3) as white crystals, with a melting point of 181.5-182.5° C. Linezolid, as well as a process for its preparation, is disclosed in U.S. Pat. No. 5,688,792 (Example 5), European Patent No. 717738, Israeli Patent No. 110,802, Canadian Patent No. 2,168,560, and International Patent Publication WO 95/07271.

This oxazolidinone is marketed in the United States by Pfizer, Inc. as an injection, tablet, and oral suspension under the name ZYVOX®. It is mainly used to treat nosocomial pneumonia, skin and skin-structure infections, and vancomycin-resistant *Enterococcus faecium* infections.

U.S. Pat. No. 5,688,792, hereinafter the '792 patent, claims linezolid and its use for the treatment of microbial infections. This patent also discloses, but does not claim, the following method of preparation:

Scheme 1

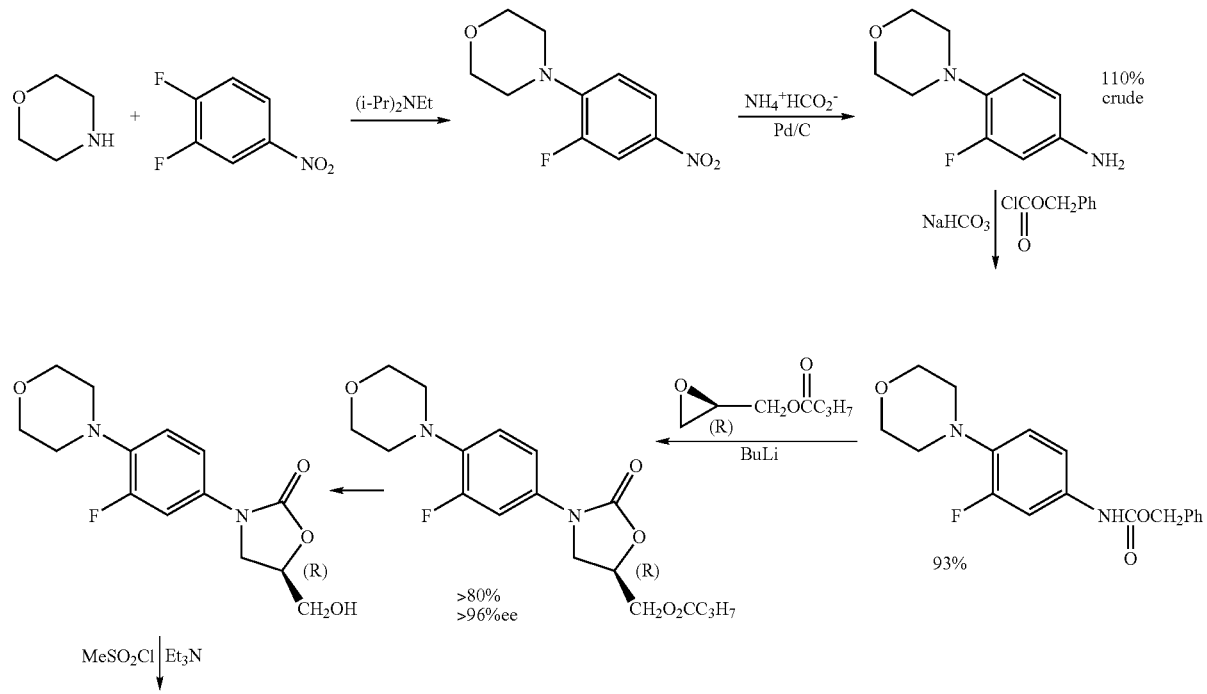

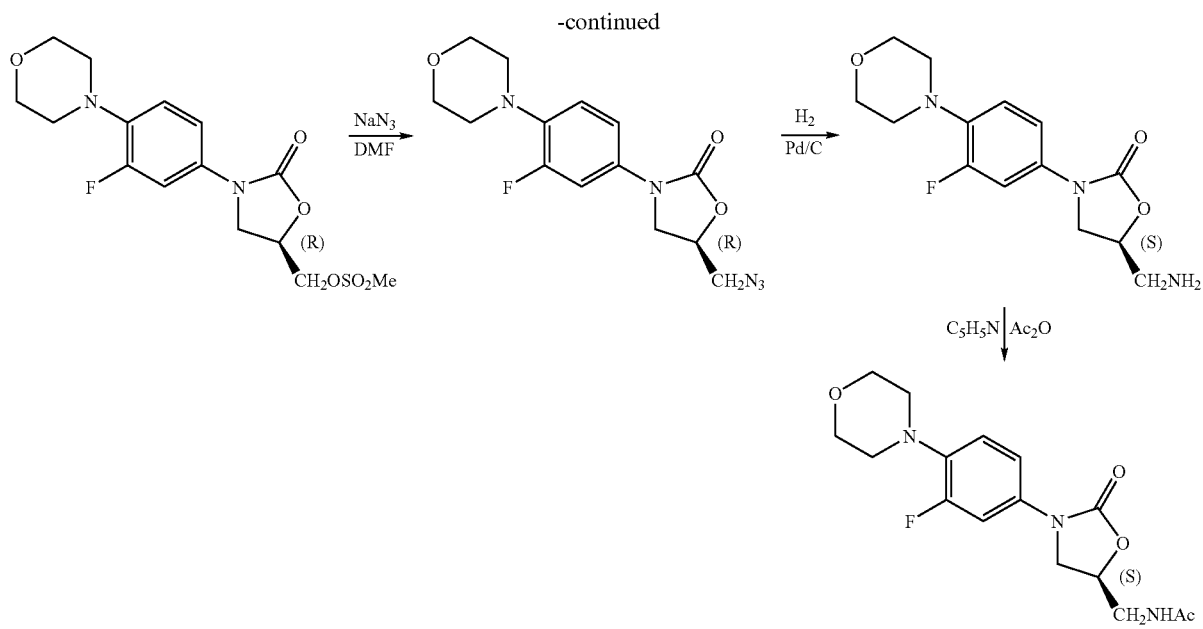

This method of preparation was also disclosed in Bricker, et al., J. Med. Chem., 39 673-679 (1996), where it was stated that the above route avoids the use of phosgene to make the carbamate precursor of the oxazolidinone ring. The authors also disclose that the use of NaN₃ can be avoided by using potassium phthalimide, followed by deblocking of the phthalimide with aqueous methyl amine.

In the above-described synthesis, the intermediate amine, S—N-(4-morpholinyl-3-fluorophenyl)-2-oxo-5-oxazolidinyl-methyl amine, having the following structure (II):

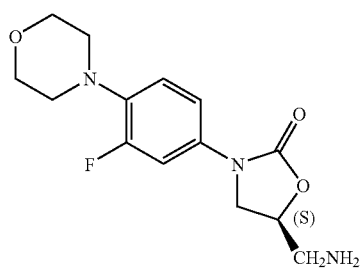

II is reacted without isolation with acetic anhydride as an oily product or in solution to produce the acetamide, linezolid (I). This is followed by procedures for isolating the linezolid such as those described in the '792 patent (col. 15, ll. 22-28) wherein a method of chromatography and separation of the desired fraction is described, followed by evaporation and trituration of the product to obtain pure linezolid. Due to the necessary treatment required for recovery, linezolid is derived in low yields.

In the above-described syntheses, the intermediate azide, R—N-(4-morpholinyl-3-fluorophenyl)-2-oxo-5-oxazolidinyl-methyl azide (III)

III is reduced to its corresponding amine, S—N-(4-morpholinyl-3-fluorophenyl)-2-oxo-5-oxazolidinyl-methyl amine (II) through catalytic hydrogenation in the presence of a palladium/carbon catalyst in the solvent ethyl acetate. These reaction conditions lead to the production of an undesirable level of reaction by-products, and thereby, following the acetylation of the intermediate amine (II) to linezolid (I), to undesirably high levels of bis-linezolid (IV).

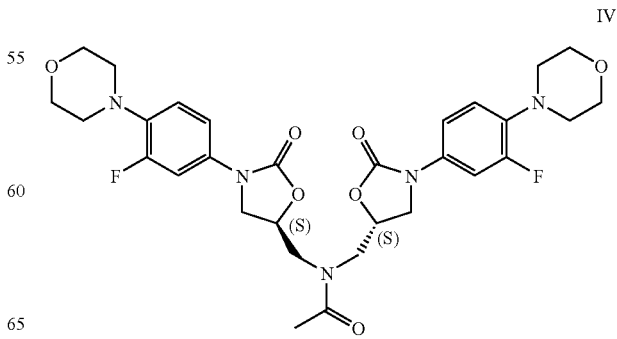

IV

It would be desirable to have a simple, efficient, industrial process for producing pure intermediate amine (II) used to then prepare linezolid (I) without the need of applying complicated and time consuming purification treatments, such as column chromatography, before the last trituration or recrystallization. The present invention provides such a method.

SUMMARY OF THE INVENTION

In one embodiment of the present invention, the reduction process is performed by catalytic hydrogenation in a process comprising:
 (a) combining R—N-(4-morpholinyl-3-fluorophenyl)-2-oxo-5-oxazolidinyl-methyl azide (III) with an organic solvent other than ethyl acetate selected from the group consisting of: $C_1$-$C_8$ linear or branched-chain aliphatic alcohols, $C_6$-$C_{12}$ aromatic hydrocarbons, mono-,di-, or tri-$C_1$-$C_4$ alkyl substituted or unsubstituted benzenes, $C_1$ to $C_4$ alkyl esters excluding ethyl acetate, and chlorinated aromatic hydrocarbons to obtain a mixture;
 (b) inducing catalytic hydrogenation of the azide (III) mixture to obtain S—N-(4-morpholinyl-3-fluorophenyl)-2-oxo-5-oxazolidinyl-methyl amine (II).

In a another embodiment of the present invention, a process is provided wherein R—N-(4-morpholinyl-3-fluorophenyl)-2-oxo-5-oxazolidinyl-methyl azide (III) is reduced to S-N-(4-morpholinyl-3-fluorophenyl)-2-oxo-5-oxazolidinyl-methyl amine (II) by a process comprising:
 (a) combining R—N-(4-morpholinyl-3-fluorophenyl)-2-oxo-5-oxazolidinyl-methyl azide (III) and a linear or branched-chain aliphatic $C_1$ to $C_8$ alcohol or a biphasic solvent system to obtain a reaction mixture; and
 (b) reduction using a reducing agent selected from the group of formic acid and salts thereof to obtain S—N-(4-morpholinyl-3-fluorophenyl)-2-oxo-5-oxazolidinyl-methyl amine (II).

In yet another embodiment, the present invention provides a process for reducing R—N-(4-morpholinyl-3-fluorophenyl)-2-oxo-5-oxazolidinyl-methyl azide (III) to S—N-(4-morpholinyl-3-fluorophenyl)-2-oxo-5-oxazolidinyl-methyl amine (II). This process comprises:
 (a) combining R—N-(4-morpholinyl-3-fluorophenyl)-2-oxo-5-oxazolidinyl-methyl azide (III) and a $C_1$ to $C_4$ alkyl ester;
 (b) reduction using a reducing agent selected from the group of borohydrides and complexes thereof in the presence of an alkaline metal base to obtain S—N-(4-morpholinyl-3-fluorophenyl)-2-oxo-5-oxazolidinyl-methyl amine (II).

In a particularly preferred embodiment, the ester used is ethyl acetate. Preferably, the reducing agent is sodium or potassium borohydride. Preferably, the base used is alkaline earth hydroxides, more preferably sodium hydroxide.

Preferably, the reduction is carried out to completion by using periodic TLC or HPLC analysis to measure when the reaction has been carried out to completion.

In yet another embodiment, the present invention provides a process for reducing R—N-(4-morpholinyl-3-fluorophenyl)-2-oxo-5-oxazolidinyl-methyl azide (III) to S—N-(4-morpholinyl-3-fluorophenyl)-2-oxo-5-oxazolidinyl-methyl amine (II). This process comprises:
 (a) combining R—N-(4-morpholinyl-3-fluorophenyl)-2-oxo-5-oxazolidinyl-methyl azide (III) and $C_1$-$C_8$ linear or branched-chain aliphatic alcohols, mono-,di-, or tri-$C_1$-$C_4$ alkyl substituted or unsubstituted benzenes, or $C_1$ to $C_4$ alkyl esters; and
 (b) reduction using a triethyl phosphite as a reducing agent to obtain S—N-(4-morpholinyl-3-fluorophenyl)-2-oxo-5-oxazolidinyl-methyl amine (II).

In another aspect of the present invention, provided are methods of preparing linezolid (I), that comprise one of the methods described above of reducing the azide (III) to the amine (II), and further the reducing the amine (II) to linezolid by methods known in the art. The linezolid obtained is of high chemical purity, with respect to the inactive R-enantiomer and bis-linezolid (IV), and is in high yield, without the need for tedious, complicated purification steps, such as chromatography.

By the process of the present invention, linezolid (I) can be produced with a content of less than about 3.2% of the bis-linezolid (IV) impurity, preferably less than about 1%, more preferably less than about 0.10%, and most preferably less than about 0.05%.

In addition, by the methods of the present invention, linezolid (I) of high purity can be produced without the need for chromatographic purification procedures. Linezolid (I) having a purity of more than about 95%, preferably more than about 98%, and most preferably more than about 99% with respect to reaction by-product impurities can be obtained by employing the methods disclosed herein.

The present invention further provides a process for preparing a pharmaceutical formulation comprising linezolid (I) having less than about 3.2% area by HPLC of bis-linezolid (IV), comprising:
 a) obtaining one or more samples of one or more batches of linezolid (I);
 b) measuring the level of bis-linezolid (IV) in each of the samples;
 c) selecting a batch of linezolid (I) having a level of bis-linezolid (IV) of less than about 3.2% area by HPLC, based on the measurement of the samples from the batches; and
 d) using the selected batch to prepare a formulation comprising linezolid (I) having less than about 3.2% area by HPLC of bis-linezolid (IV).

DETAILED DESCRIPTION OF THE INVENTION

As used herein, room temperature and is meant to indicate a temperature of about 18 to about 25° C., preferably about 20 to about 22° C.

As used herein, a biphasic solvent system can be a mixture of an organic solvent and an aqueous solvent. Preferably, the aqueous solvent is water. The ratio of organic solvent:water can be from about 0.1:1 to about 10:1, with a ratio of about 1:1 being preferred. The phase transfer agent can be selected from a wide variety of known phase transfer agents, including tetrabutylammonium bromide (TBAB).

The present invention relates to novel and improved methods for the reduction of R—N-(4-morpholinyl-3-fluorophenyl)-2-oxo-5-oxazolidinyl-methyl azide (III), to its corresponding amine, S—N-(4-morpholinyl-3-fluorophenyl)-2-oxo-5-oxazolidinyl-methyl amine (II).

As used herein, the conversion of the azide (—$N_3$) group to the amine (—$NH_2$) group is by a reduction reaction. In this context, the reduction reaction can comprise catalytic hydrogenation, for example, see Sheradsky, T. in *The Chemistry of the Azido Group*, Patai, S. Ed., Interscience Press (1971), Chapter 6, p. 331, or use of another reducing agent.

Disclosed in the '792 patent, Example 5 therein, is a procedure for the preparation of linezolid, wherein reduction of the corresponding azide (III) to the corresponding amine (II) is by hydrogenation, using ethyl acetate as the solvent. In contradistinction, the present invention discloses a process for reduction wherein hydrogenation is carried out in the absence of the solvent ethyl acetate, or using ammonium formate as a reducing agent in a variety of solvents or solvent systems.

In one embodiment of the present invention, the reduction process is performed by catalytic hydrogenation in a process comprising:
(a) combining R—N-(4-morpholinyl-3-fluorophenyl)-2-oxo-5-oxazolidinyl-methyl azide (III) with an organic solvent other than ethyl acetate selected from the group consisting of: $C_1$-$C_8$ linear or branched-chain aliphatic alcohols, $C_6$-$C_{12}$ aromatic hydrocarbons, and mono-, di-, tri-$C_1$-$C_4$ alkyl substituted or unsubstituted benzenes, $C_1$ to $C_4$ alkyl esters excluding ethyl acetate and chlorinated aromatic hydrocarbons to obtain a mixture;
(b) inducing catalytic hydrogenation of the said azide (III) mixture to obtain S—N-(4-morpholinyl-3-fluorophenyl)-2-oxo-5-oxazolidinyl-methyl amine (II).

In this process, ethyl acetate is not present in such an amount as to function as a solvent or co-solvent. The absence of ethyl acetate is not intended to include situations where ethyl acetate is present in trace amounts or in amounts small enough to be insignificant in terms of functioning as a solvent. The most preferred organic solvent in step (a) is toluene. Preferably, the organic solvent is in an amount of about 28 to about 40 volumes, more preferably about 35 volumes (g/mL) in order to obtain complete dissolution. These volumes are less than those mentioned in the '792 patent and thus provide an advantage.

Preferably, when combining the azide with the organic solvent in step (a), complete dissolution is obtained.

Catalytic hydrogenation of azides in general are known in the art and is typically performed by flushing the reaction mixture 3 times with nitrogen and 3 times with hydrogen at 1.5 atm, while maintaining a temperature of about −5° C. to about 35° C., preferably room temperature. The catalytic hydrogenation is preferably carried out to completion by using periodic TLC or HPLC analysis.

This reduction reaction is conducted in the presence of a catalyst. Catalysts used are noble metal catalysts, such as platinum, palladium. Preferably the noble metal catalyst is palladium. The noble metal catalyst may be provided on an inert support such as carbon, activated carbon or alumina. Preferably, the noble metal catalyst is palladium on carbon ("Pd/C"). Preferably, the noble metal catalyst is an amount of about 2-20% compared to the azide.

Preferably, the catalytic hydrogenation reaction is conducted in the presence of any form of ammonium, including aqueous and gaseous form, water, a $C_1$ to $C_2$ alcohol, water or sodium hydroxide which is added to the reaction mixture in step (a). Preferably, ammonia gas is bubbled or ammonium hydroxide is admixed into the reaction mixture in step (a).

Once obtaining the S—N-(4-morpholinyl-3-fluorophenyl)-2-oxo-5-oxazolidinyl-methyl amine (II) in step (b), recovery may be performed by any method known in the art. Preferably, the recovery is performed by filtering, more preferably through a celite filter and removal of the solvent.

In a another embodiment of the present invention, a process is provided wherein R—N-(4-morpholinyl-3-fluorophenyl)-2-oxo-5-oxazolidinyl-methyl azide (III) is reduced to S—N-(4-morpholinyl-3-fluorophenyl)-2-oxo-5-oxazolidinyl-methyl amine by a process comprising:
(a) combining R—N-(4-morpholinyl-3-fluorophenyl)-2-oxo-5-oxazolidinyl-methyl azide (III) and a linear or branched-chain aliphatic $C_1$ to $C_8$ alcohol or a biphasic solvent system to obtain a reaction mixture; and
(b) reduction using a reducing agent selected from the group of formic acid and salts thereof to obtain S—N-(4-morpholinyl-3-fluorophenyl)-2-oxo-5-oxazolidinyl-methyl amine (II).

Preferably, the organic solvent is in an amount of about 10 to about 25 volumes, more preferably about 15 volumes (g/mL). In known prior art processes, larger amounts of solvents are used in order to obtain complete dissolution.

The most preferred solvent in step (a) is ethanol or butanol. Preferably, the reducing agent is ammonium formate.

This reduction reaction is conducted in the presence of a catalyst. Catalysts used are zinc or noble metal catalysts, such as platinum, palladium. Preferably the noble metal catalyst is palladium. The noble metal catalyst may be provided on an inert support such as carbon, activated carbon or alumina. Preferably, the noble metal catalyst is palladium on carbon ("Pd/C"). Preferably, the noble metal catalyst is in an amount of about 2-20% compared to the azide while the zinc is in an amount of about 1 to 2 equivalents, relative to the azide.

Preferably, the reduction is carried out to completion, as judged using periodic TLC or HPLC analysis.

Once obtaining the S—N-(4-morpholinyl-3-fluorophenyl)-2-oxo-5-oxazolidinyl-methyl amine (II) in step (b), recovery may be performed by any method known in the art. Preferably, the recovery is performed by filtering, more preferably through a celite filter and removal of the solvent.

In yet another embodiment, the present invention provides a process for reducing R—N-(4-morpholinyl-3-fluorophenyl)-2-oxo-5-oxazolidinyl-methyl azide (III) to S—N-(4-morpholinyl-3-fluorophenyl)-2-oxo-5-oxazolidinyl-methyl amine (II). This process comprises:
(a) combining R—N-(4-morpholinyl-3-fluorophenyl)-2-oxo-5-oxazolidinyl-methyl azide (III) and a $C_1$ to $C_4$ alkyl ester;
(b) reduction using a reducing agent selected from the group of borohydrides and complexes thereof in the presence of an alkaline metal base to obtain S—N-(4-morpholinyl-3-fluorophenyl)-2-oxo-5-oxazolidinyl-methyl amine (II).

In a particularly preferred embodiment, the ester used is ethyl acetate. Preferably, the reducing agent is sodium or potassium borohydride. Preferably, the base used is alkaline earth hydroxides, more preferably sodium hydroxide.

Preferably, the reduction is carried out to completion by using periodic TLC or HPLC analysis to measure when the reaction has been carried out to completion.

In yet another embodiment, the present invention provides a process for reducing R—N-(4-morpholinyl-3-fluorophenyl)-2-oxo-5-oxazolidinyl-methyl azide (III) to S—N-(4-morpholinyl-3-fluorophenyl)-2-oxo-5-oxazolidinyl-methyl amine (II). This process comprises:
(a) combining R—N-(4-morpholinyl-3-fluorophenyl)-2-oxo-5-oxazolidinyl-methyl azide (III) and a $C_1$-$C_8$ linear, mono-,di-, tri-$C_1$-$C_4$ alkyl substituted or unsubstituted benzenes, $C_1$ to $C_4$ alkyl esters or branched-chain aliphatic alcohol.
(b) reduction using a triethyl phosphite as a reducing agent to obtain S—N-(4-morpholinyl-3-fluorophenyl)-2-oxo-5-oxazolidinyl-methyl amine (II).

Preferably R—N-(4-morpholinyl-3-fluorophenyl)-2-oxo-5-oxazolidinyl-methyl azide (III) is combined with a toluene, benzene or ethyl acetate while toluene is more preferable.

Preferably, the reduction is carried out to completion by using periodic TLC or HPLC analysis to measure when the reaction has been carried out to completion.

In another aspect of the present invention, provided are methods of preparing linezolid, that comprise one of the methods described above of reducing the azide (III) to the amine (II), and further reducing the amine (II) to linezolid by methods known in the art. The linezolid obtained is of high chemical purity, with respect to the inactive R-enantiomer and bis-linezolid, and is in high yield, without the need for tedious, complicated purification steps, such as chromatography.

In a preferred embodiment of this process, a one pot process is provided wherein the amine (II) is not precipitated from the reduction reaction mixture but rather is converted directly in the solution to linezolid by acetylation. Even without precipitation and/or further purification of the amine (II), linezolid (I) free of undesirable levels of impurities so as not to require purification by such means as chromatography, can be produced.

When linezolid (I) is produced by the process of the present invention, it is in high purity and substantially free of by-products and undesirable levels of impurities such as bis-linezolid. In addition, the ability to produce pure intermediate amine (II) by the methods of the present invention avoids the need for tedious, expensive, and time consuming purification steps. In published procedures of preparing linezolid, purification steps are needed after the acetylation step that converts the amine to linezolid. This requires a tedious chromatography procedure and separation of the desired fraction, followed by evaporation and trituration of the product to obtain pure linezolid (see, e.g., U.S. Pat. No. 5,688,792, at col. 15, 11. 22-28). Such manipulations are time consuming, expensive, and inevitably decrease yield.

By the process of the present invention, linezolid (I) can be produced with a content of less than about 3.2% of the bis-linezolid impurity, preferably less than about 1%, more preferably less than about 0.10%, and most preferably less than about 0.05%.

In addition, by the methods of the present invention, linezolid (I) of high purity can be produced without the need for chromatographic purification procedures. Linezolid (I) having a purity of more than about 95%, preferably more than about 98%, and most preferably more than about 99% with respect to reaction by-product impurities can be obtained by employing the methods disclosed herein.

The present invention further provides a process for preparing a pharmaceutical formulation comprising linezolid (I) having less than about 3.2% area by HPLC of bis-linezolid (IV), comprising:

(a) obtaining one or more samples of one or more batches of linezolid (I);
(b) measuring the level of the compound of bis-linezolid (IV) in each of the samples;
(c) selecting a batch of linezolid (I) having a level of bis-linezolid (IV) of less than about 3.2% area by HPLC, based on the measurement of the samples from the batches; and
(d) using the selected batch to prepare a formulation comprising linezolid (I) having less than about 3.2% area by HPLC of bis-linezolid (IV).

Preferably, the bis-linezolid content is less than about 0.25% area by HPLC. More preferably, less than about 0.10%, and most preferably less than about 0.05%.

If the level of the bis-linezolid measured in step b) is higher than about 3.2% area by HPLC, it may be reduced by crystallization from ethyl acetate.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

Example 1

Comparative Example, Based on U.S. Pat. No. 5,688,792 Preparation of Linezolid from Azide (III) Intermediate by Catalytic Hydrogenation In a 1L reactor, 6 g R—N-(4-morpholinyl-3-fluorophenyl)-2-oxo-5-oxazolidinyl-methyl azide (III) was charged with 150 ml ethyl acetate, followed by 0.6 g Pd/C. The system was flushed 3 times with nitrogen and 3 times with hydrogen. The pressure of hydrogen was set to 1.5 atm. The reaction mixture was stirred at RT and the reaction followed by TLC or HPLC until completion. The reaction mixture was filtered through celite and the solution was treated with acetic anhydride in the presence of triethyl amine at RT. The precipitate was filtered and dried to obtain linezolid (I) crystalline Form IV with a 3.2% content of bis-linezolid (IV).

Example 2

Preparation of Linezolid from Azide (III) Intermediate by Catalytic Hydrogenation In a 1L reactor, 9 g R—N-(4-morpholinyl-3-fluorophenyl)-2-oxo-5-oxazolidinyl-methyl azide (III) was charged with 150 ml toluene, followed by 0.6 g Pd/C and 20 ml ammonium hydroxide. The system was flushed 3 times with nitrogen and 3 times with hydrogen. The pressure of hydrogen was set to 1.5 atm. The reaction mixture was stirred at RT and the reaction followed by TLC or HPLC until completion. The reaction mixture was filtered through celite and the solution was treated with 1.5 to 5 equivalents of acetic anhydride at RT. The precipitate formed was filtered and dried to obtain linezolid (I) No traces of bis-linezolid (4) were detected, indicating not more than 0.01% (w/w) bis-linezolid (4).

Example 3

Preparation of Linezolid Free of the (R)-Linezolid Enantiomer from Azide (III) Intermediate by Catalytic Hydrogenation and Ammonium Hydroxide In a 10L reactor, 150 g R—N-(4-morpholinyl-3-fluorophenyl)-2-oxo-5-oxazolidinyl-methyl azide (III) was charged, followed by 15 g Pd/C in 5L toluene. Finally, 500 ml ammonium hydroxide was added. The system was flushed 3 times with nitrogen and 3 times with hydrogen. The pressure of hydrogen was set to 1.5 atm. The reaction mixture was stirred at RT and the reaction followed by TLC or HPLC until completion. The reaction mixture was filtered through celite.

To the solution containing the obtained (S)-N-(4-morpholinyl-3-fluorophenyl)-2-oxo-5-oxazolidinyl-methylamine (II) formed above, acetic anhydride was added drop wise (2 equivalents). The reaction mixture was stirred during 4 hours at RT. During this period, linezolid (I) crystals were precipitated. The crystals were filtered and dried. (% R-enantiomer of linezolid: 0.6% (w/w).

Example 4

Preperation of Linezolid Free the (R)-Linezolid Enantiomer from Azide (III) Intermediate by Catalytic Hydrogenation and Ammonium Gas In a 10L reactor, 150 g R—N-(4-morpholinyl-3-fluorophenyl)-2-oxo-5-oxazolidinyl-methyl azide (III) was charged with 5L toluene, followed by 15 g Pd/C (10% Pd/C containing 52% water). The system was bubbled with ammonia (gas) during 2 h, then flushed 3 times with nitrogen and 3 times with hydrogen. The pressure of hydrogen was set to 1.5 atm. The reaction mixture was stirred at RT and the reaction followed until completion. The reaction mixture was filtered through celite and the solution was treated with 60 ml acetic anhydride at RT. The precipitate was filtered and dried to obtain linezolid (I) crystalline Form IV (purity: 99.5%, yield: 91%).

Example 5

Preperation of Intermediate Amine (II) by Catalytic Hydrogenation

In a 10L reactor, 150 g R—N-(4-morpholinyl-3-fluorophenyl)-2-oxo-5-oxazolidinyl-methyl azide (III) was charged, followed by 15 g Pd/C in 5L toluene. Finally 500 ml ammonium hydroxide was added. The system was flushed 3 times with nitrogen and 3 times with hydrogen. The pressure of hydrogen was set to 1.5 atm. The reaction mixture was stirred at RT and the reaction followed by TLC or HPLC until completion. The reaction mixture was filtered through celite. S—N-(4-morpholinyl-3-fluorophenyl)-2-oxo-5-oxazolidinyl-methyl amine (II) precipitated on standing and/or cooling as a white solid, was filtered, and dried at 50° C. overnight. (Form C, 98.6% total purity by HPLC).

Example 6

Preperation of Linezolid from Azide (III) Intermediate by Catalytic Hydrogenation In a 10L reactor, 150 g R—N-(4-morpholinyl-3-fluorophenyl)-2-oxo-5-oxazolidinyl-methyl azide (III) was charged with 5L toluene, followed by 15 g Pd/C (10% Pd/C containing 52% water). The system was bubbled with ammonia (gas) during 2 h, then flushed 3 times with nitrogen and 3 times with hydrogen. The pressure of hydrogen was set to 1.5 atm. The reaction mixture was stirred at RT and the reaction followed by TLC or HPLC until completion. The reaction mixture was filtered through celite and the solution was treated with 60 ml acetic anhydride at RT. The precipitate was filtered and dried to obtain crystalline linezolid (I) (purity: 99.5%, yield: 91%).

Example 7

Preperation of Linezolid from Azide (III) Intermediate by Catalytic Hydrogenation In a 10L reactor, 150 g R—N-(4-morpholinyl-3-fluorophenyl)-2-oxo-5-oxazolidinyl-methyl azide were charged followed by 7.5 g Pd/C in 5.25L toluene. Finally, ammonia was bubbled for 1 hr. The system was flushed three times with nitrogen and 3 times with hydrogen. The pressure of hydrogen was set to 1.7 atm. The reaction mixture was stirred at RT and the reaction followed up until completion. The reaction mixture was filtered. The toluene was distillated out to dryness.

4.5L ethyl acetate were added to the residual (S)-N-(4-morpholinyl-3-fluorophenyl)-2-oxo-5-oxazolidinyl-methylamine The mixture was heated until dissolution and filtered. To the solution, acetic anhydride was added drop wise (at least 2.5 equivalents). The reaction mixture was stirred over 2 hours at RT (until completion, if needed more acetic anhydride is added). During this period, linezolid was precipitated. The crystals were filtered and dried (Form IV). No further purification is needed.

Example 8

Preperation of Intermediate Amine (II) Using Ammonium Formate

In a three necked flask, 6.4 g R—N-(4-morpholinyl-3-fluorophenyl)-2-oxo-5-oxazolidinyl-methyl azide (III) was charged, followed by 2.5 g ammonium formate, 23 ml ethanol, and 2.6 g zinc powder. The reaction mixture was stirred at RT and the reaction followed by TLC or HPLC until completion. 60 ml acetone was then added. The reaction mixture was filtered and by evaporation S—N-(4-morpholinyl-3-fluorophenyl)-2-oxo-5-oxazolidinyl-methyl amine (II) was obtained as a solid. (Form A, 96.5% total purity by HPLC).

Example 9

Preperation of Linezolid Free of the (R)-Linezolid enantiomer and Bis-Linezolid (4) from Azide (III) Intermediate Using Reducing Agent: Ammonium Formate (and Ammonium Hydroxide)

In a three-necked flask, 6.4 g R—N-(4-morpholinyl-3-fluorophenyl)-2-oxo-5-oxazolidinyl-methyl azide (III) was charged, followed by 100 ml butanol, 2.5 g ammonium formate, and 1.3 g 10% palladium over charcoal. The reaction mixture was stirred at 80° C. during 6 h. The reaction mixture was filtered. To the organic solution, 4 ml triethyl amine was added and the mixture was cooled to 0° C. 4.7 ml acetic anhydride was added dropwise. Linezolid (I) precipitated from the reaction mixture and was filtered off. 2.45 g dry linezolid (I) Form IV was obtained (purity: 93.2%; 50% yield).

Example 10

Preperation of Linezolid from Azide (III) Intermediate Using Reducing Agent: Ammonium Formate In a three necked flask, 6.4 g R—N-(4-morpholinyl-3-fluorophenyl)-2-oxo-5-oxazolidinyl-methyl azide (III) was charged, followed by 2.5 g ammonium formate, 2.6 g zinc powder, 0.6 g TBAB, and 100 ml of a 1:1 mixture ethyl acetate: water. The reaction mixture was stirred at RT during 2 h, and then heated to reflux for 10 h. The reaction mixture was filtered. The phases were separated; the aqueous phase was extracted twice with ethyl acetate. All the organic phases were combined, 4 ml triethyl amine was added and the mixture was cooled to 0° C. 4.7 ml acetic anhydride was added drop wise. The reaction mixture was stirred overnight. 3.6 g dry linezolid (I) were obtained (purity: 98.7%, 54% yield).

Example 11

Preperation of Linezolid from Azide (III) Intermediate Using Reducing Agent: Sodium Borohydride In a three necked flask, 10 g R—N-(4-morpholinyl-3-fluorophenyl)-2-oxo-5-oxazolidinyl-methyl azide (III) was charged, followed by 1 g TBAB, 2 g $NaBH_4$, 1 g NaOH pellets, and 100 ml ethyl acetate under a nitrogen atmosphere. The reaction mixture was maintained at 55° C. overnight. Water was added and the phases were separated. The aqueous phase was washed twice with ethyl acetate. The organic phases were combined. Triethyl amine (10 ml) was added to the solution, followed by 10 ml of acetic anhydride. The solution was stirred overnight. 30 ml petroleum ether was added, inducing precipitation of crystalline linezolid (I). 2.6 g white crystals were obtained (purity: 96.2% yield: 35%).

Example 12

Preperation of Linezolid from Amine (II) Intermediate Using Acetic Anhydride 200 ml toluene at 25° C. was added to a flask containing 29 g of crystalline (S)-N-(4-morpholinyl-3-fluorophenyl)-2-oxo-5-oxazolidinyl-methyl amine (II). Acetic anhydride (2.5 equivalents) was added dropwise. The reaction mixture was stirred overnight. Linezolid (I) that precipitated from the reaction mixture was filtered. The precipitate was dried at 50° C. in an oven overnight. The crystals obtained were analyzed by PXRD and showed linezolid (I) Form IV. The yield was 84.9% and the (R)-linezolid enantiomer content found was 0.03%. Furthermore, no traces of bis-linezolid (IV) were detected, indicating not more than 0.01% (w/w) bis-linezolid (IV).

Example 13

Preperation of Linezolid Form IV Free of Bis-Linezolid (IV) and the (R)-Linezolid Enantiomer from Amine (II) Intermediate Using Acetic Anhydride To the solution containing the obtained (S)—N-(4-morpholinyl-3-fluorophenyl)-2-oxo-5-oxazolidinyl-methylamine (II), acetic anhydride was added drop wise (2 equivalents). The reaction mixture was stirred during 4 hours at RT. During this period, crude linezolid (I) was precipitated. The crystals were filtered and dried (% R-enantiomer of linezolid: 0.6% (w/w).

Example 14

Preperation of Linezolid from Amine (II) Intermediate Using Ethyl Acetate 3 g of S—N-(4-morpholinyl-3-fluorophenyl)-2-oxo-5-oxazolidinyl-methyl amine (II) was mixed with 50 ml ethyl acetate. 3 ml triethyl amine was added and the mixture was cooled to 0° C. 2.5 ml acetic anhydride was added drop wise. The reaction mixture was stirred overnight. 2.5 g dry linezolid (I) Form IV was obtained (purity: 98.3% yield: 70%).

Example 15

Batch Method

Linezolid (1.7 g, containing 3.15% bis-linezolid) was mixed with ethyl acetate (110 ml, 66V) and heated to reflux. The turbid solution was filtered while hot to obtain a clear solution. By cooling until room temperature, the crystals were filtered and dried. 1.22 g (71.3% yield) were obtained and analyzed for their bis-linezolid content. bis-linezolid was 0.02%.

Linezolid (15 g, containing 0.16% bis-linezolid) was mixed with ethyl acetate (450 ml, 30V) and heated to reflux. The turbid solution was filtered while hot to obtain a clear solution. By cooling until room temperature, the crystals were filtered and dried. 12.5 g (83.3% yield) were obtained and analyzed for their bis-linezolid content. bis-linezolid was not detected.

HPLC method

Column Hypersil Gold 150×4.6, 5µ

Detection limit: 0.1%

Eluents: 0.01M $K_2HPO_4$: MeOH A: 80:20 B: 50:50

TABLE 1

| Time | A | B | Flow |
|---|---|---|---|
| 0 | 100 | 0 | 1.5 |
| 15 | 57 | 43 | 2 |
| 25 | 35 | 65 | 2 |

We claim:

1. A process for preparation of S—N-(4-morpholinyl-3-fluorophenyl)-2-oxo-5-oxazolidinyl-methyl amine (II) from R—N-(4-morpholinyl-3-fluorophenyl)-2-oxo-5-oxazolidinyl-methyl azide (III) by catalytic hydrogenation comprising:
   (a) combining R—N-(4-morpholinyl-3-fluorophenyl)-2-oxo-5-oxazolidinyl-methyl azide (III) with an organic solvent other than ethyl acetate selected from the group consisting of:
      $C_6$-$C_{12}$ aromatic hydrocarbons, mono-,di-, or tri-$C_1$-$C_4$ alkyl substituted or unsubstituted benzenes, and chlorinated aromatic hydrocarbons to obtain a mixture; and
   (b) inducing catalytic hydrogenation of the said azide (III) mixture to obtain S—N-(4-morpholinyl-3-fluorophenyl)-2-oxo-5-oxazolidinyl-methyl amine (II).

2. The process in claim 1, wherein the combining in step (a) is until complete dissolution.

3. The process in claim 1, wherein the organic solvent in step (a) is toluene.

4. The process in claim 1, wherein the organic solvent is in an amount of about 28 to about 40 volumes (g/mL).

5. The process in claim 4, wherein the organic solvent is in an amount of about 35 volumes (g/mL).

6. The process in claim 1, wherein catalytic hydrogenation is carried out to completion by using periodic TLC or HPLC analysis.

7. The process in claim 1, wherein catalytic hydrogenation conducted in the presence of a noble metal catalyst.

8. The process in claim 7, wherein the noble metal catalyst is platinum or palladium.

9. The process in claim 7, wherein catalytic hydrogenation conducted in the presence of a noble metal catalyst on an inert support such as carbon, activated carbon or alumina.

10. The process in claim 9, wherein the noble metal catalyst is palladium on carbon ("Pd/C").

11. The process in claim 7, wherein the noble metal catalyst is in an amount of about 2 to about 20% compared to the azide.

12. The process in claim 1, wherein catalytic hydrogenation is conducted in the presence of any form of ammonium, including aqueous and gaseous form, water, sodium hydroxide or a $C_1$ to $C_2$ alcohol, water or sodium hydroxide.

13. The process in claim 12, wherein catalytic hydrogenation is conducted in the presence of ammonia gas or ammonium hydroxide.

14. The process in claim 1 further comprising converting the amine (II) into linezolid (I).

15. The process of claim 14, wherein the linezolid (I) produced comprises less than about 3.2% of bis-linezolid (IV).

16. The process of claim 14, wherein the linezolid (I) produced comprises less than about 1% of bis-linezolid (IV).

17. The process of claim 14, wherein the linezolid (I) produced comprises less than about 0.1% of bis-linezolid (IV).

18. The process of claim 14, wherein the linezolid (I) produced comprises less than about 0.05% of bis-linezolid (IV).

19. The process of claim 14, wherein pure linezolid (I) is produced having a purity of more than about 95% with respect to reaction by-product impurities.

20. The process of claim 14, wherein pure linezolid (I) is produced having a purity of more than about 98% with respect to reaction by-product impurities.

21. The process of claim 14, wherein pure linezolid (I) is produced having a purity of more than about 99% with respect to reaction by-product impurities.

* * * * *

UNITED STATES PATENT AND TRADEMARK OFFICE
CERTIFICATE OF CORRECTION

PATENT NO.       : 7,291,614 B2
APPLICATION NO. : 11/361457
DATED           : November 6, 2007
INVENTOR(S)     : Fine et al.

It is certified that error appears in the above-identified patent and that said Letters Patent is hereby corrected as shown below:

Column 1, line 28-29, change
"[(S)-N-[[3-(3-Fluoro-4-morpholinyl)phenyl]-2-oxo-5-oxazolidinyl]methyl] acetamide]"

to -- [(S)-N-[[3-(3-fluoro-4-morpholinyl)phenyl]-2-oxo-5-oxazolidinyl]methyl] acetamide] --

Column 1-2, scheme 1 change " " to --  --

Column 3, line 28-29, change "Bricker, et al., J. Med. Chem., 39 673 – 679 (1996)"
to -- Bricker, et al., *J. Med. Chem.*, `(1996) 39 673 – 679 --

Column 5, line 25, change "in a another" to -- in another --

Column 6, line 45, change "18 to about 25°_C." to -- 18° to about 25°C --

Column 6, line 46, change "20 to about 25°_C." to -- 20° to about 25°C --

Column 10, line 66-67, change
"(S)-N-(4-morpholinyl-3-fluorophenyl)-2-oxo-5-oxazolidinyl-methy" to
-- (S)-N-(4-morpholinyl-3-fluorophenyl)-2-oxo-5-oxazolidinyl-methyl --

Column 11, line 1, change "lamine" to -- amine --

Column 11, line 9, change "Preperation" to -- Preparation --

Column 11, line 27, change "Preperation" to -- Preparation --

Column 11, line 45, change "Preperation" to -- Preparation --

Column 11, line 63, change "Preperation" to -- Preparation --

Column 12, line 7-9, change
"(S)-N-(4-morpholinyl-3-fluorophenyl)-2-oxo-5-oxazolidinyl-methy- lamine" to
-- (S)-N-(4-morpholinyl-3-fluorophenyl)-2-oxo-5-oxazolidinyl-methyl-amine --

CERTIFICATE OF CORRECTION (continued)
U.S. Pat. No. 7,291,614 B2

Column 12, line 18, change "Preperation" to -- Preparation --

Column 12, line 35, change "Preperation" to -- Preparation --

Column 12, line 54, change "Preperation" to -- Preparation --

Column 13, line 7, change "Preperation" to -- Preparation --

Column 13, line 27, change "Preperation" to -- Preparation --

Column 13, line 46, change "Preperation" to -- Preparation --

Column 13, line 61, change "Preperation" to -- Preparation --

Column 13, line 46, change "Preperation" to -- Preparation --

Column 14, line 23, change "HPLC Method" to -- HPLC Method --

Signed and Sealed this

Sixteenth Day of March, 2010

David J. Kappos
*Director of the United States Patent and Trademark Office*